United States Patent
Yonezu et al.

(10) Patent No.: US 10,393,715 B2
(45) Date of Patent: Aug. 27, 2019

(54) GAS SENSOR HAVING A TUBULAR BODY TIGHTLY FITTED TO A TAPERED PORTION OF A METALLIC SHELL

(71) Applicant: NGK SPARK PLUG CO., LTD., Nagoya-shi, Aichi (JP)

(72) Inventors: Kunihiko Yonezu, Inuyama (JP); Takehiro Oba, Konan (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 231 days.

(21) Appl. No.: 15/481,197

(22) Filed: Apr. 6, 2017

(65) Prior Publication Data

US 2017/0307574 A1    Oct. 26, 2017

(30) Foreign Application Priority Data

Apr. 21, 2016 (JP) ................................. 2016-085220

(51) Int. Cl.
*G01N 33/00* (2006.01)

(52) U.S. Cl.
CPC ................................ *G01N 33/0036* (2013.01)

(58) Field of Classification Search
CPC ........... G01N 33/0036; G01N 27/4077; G01N 27/409; G01N 33/0009; G01N 7/00
See application file for complete search history.

(56) References Cited

U.S. PATENT DOCUMENTS

| 9,335,311 B2 * | 5/2016 | Yonezu | G01N 27/4062 |
| 2008/0277282 A1 * | 11/2008 | Kume | G01N 27/4077 204/424 |
| 2009/0214389 A1 * | 8/2009 | Miyata | G01N 27/407 422/83 |
| 2010/0050740 A1 * | 3/2010 | Matsubara | G01N 27/4077 73/23.31 |
| 2010/0170794 A1 * | 7/2010 | Gibson | G01N 27/4062 204/406 |
| 2011/0239739 A1 * | 10/2011 | Katou | G01N 27/4078 73/31.05 |

FOREIGN PATENT DOCUMENTS

JP    2009-198422 A    9/2009

* cited by examiner

*Primary Examiner* — Harshad R Patel
*Assistant Examiner* — Nigel H Plumb
(74) *Attorney, Agent, or Firm* — Stites & Harbison, PLLC; Jeffrey A. Haeberlin; James R. Hayne

(57) ABSTRACT

A gas sensor includes a gas sensor element having a detection portion, a metallic shell holding the gas sensor element, and a tubular body made of metal, which is welded in a state of being externally fitted to a front side or a rear side of the metallic shell. In the present invention, the tubular body is tightly fitted to a tapered portion that is provided at an outer surface of the metallic shell and is radially narrowed toward the tubular body. The tubular body is welded at the tapered portion.

4 Claims, 6 Drawing Sheets

GAS SENSOR HAVING A TUBULAR BODY TIGHTLY FITTED TO A TAPERED PORTION OF A METALLIC SHELL

CROSS REFERENCE TO RELATED APPLICATION

The present application claims priority to Japanese Patent Application No. 2016-085220, which was filed on Apr. 21, 2016, the disclosure of which is herein incorporated by reference in its entirety.

BACKGROUND OF THE INVENTION

Field of the Invention

The present invention relates to a gas sensor including a gas sensor element for detecting the concentration of a gas under measurement.

Description of Related Art

Hitherto, a gas sensor is mounted to an intake system (e.g., an intake pipe or an intake manifold) of an internal combustion engine such as a diesel engine or a gasoline engine, and the concentration of a specific gas is monitored by the gas sensor to control the condition of combustion or the like. In this gas sensor, a gas detection element is held in a metallic shell, a front end portion of the gas detection element, which protrudes frontward relative to the metallic shell, is covered with a tubular protector made of metal, and a rear end portion of the gas detection element, which protrudes rearward relative to the metallic shell, is covered with a sleeve made of metal (Patent Document 1).

The sleeve is connected to the metallic shell in a manner as shown in FIGS. 7A to 7C, for example.

First, a front end side of a sleeve 1100 is press-fitted to a rear end portion of a metallic shell 500 (FIG. 7A). At this time, since an inner diameter d0 of the sleeve 1100 is smaller than an outer diameter dx of the rear end portion of the metallic shell 500, the press-fitting is performed while increasing the diameter of the sleeve 1100 to the outer diameter dx at a predetermined press-fitting load. Then, the sleeve 1100, the diameter of which has been increased to the outer diameter dx, is further press-fitted to the metallic shell 500 (FIG. 7B). The sleeve 1100 is press-fitted while sliding along an outer surface 500e of the metallic shell 500.

When a front end portion 1100f of the sleeve 1100 comes into contact with a flange portion 570 of the metallic shell 500, the sleeve 1100 is positioned in the depth direction of the press-fitting. In this state, the press-fitting (temporary fixing) of the sleeve 1100 to the metallic shell 500 is ended. Finally, a welded portion W is formed by all-around welding performed from the outside of the press-fitted portion of the sleeve 1100 to complete the fixing (FIG. 7C).

RELATED ART DOCUMENT

Patent Document 1 is Japanese Patent Application Laid-Open (kokai) No. 2009-198422 (FIG. 1, FIG. 3).

BRIEF SUMMARY OF THE INVENTION

Meanwhile, if the above-mentioned press-fitting load exceeds the buckling strength of the sleeve 1100, the sleeve 1100 may be broken. Therefore, when the press-fitting load is likely to be increased, the press-fitting load has to be reduced by annealing the sleeve 1100 in advance. Alternatively, fixing by crimping, in which the sleeve 1100 is crimped from the radially outer side toward the radially inner side, has to be used instead of the press-fitting. Both methods lead to reduction in productivity and/or increase in cost.

Therefore, an object of the present invention is to provide a gas sensor capable of reducing a press-fitting load when a tubular body made of metal is externally fitted to a metallic shell that holds a gas sensor element.

In order to solve the above problems, a gas sensor of the present invention includes: a gas sensor element extending in a direction of an axis, and including, at a front side thereof, a detection portion configured to detect a specific gas component in a measurement target gas; a metallic shell surrounding a radial periphery of the gas sensor element, and holding the gas sensor element; and a tubular body made of metal, which is welded in a state of being externally fitted to a front side or a rear side of the metallic shell. The tubular body is tightly fitted to a tapered portion that is provided at the outer surface of the metallic shell and is radially narrowed toward the tubular body. The tubular body is welded at the tapered portion.

According to this gas sensor, the tapered portion that is radially narrowed toward the tubular body is formed at the outer surface of the metallic shell on the front side or the rear side of the metallic shell. When the tubular body is externally fitted (press-fitted), the diameter of the tubular body is gradually increased along the surface of the tapered portion. Therefore, in contrast to the case where press-fitting of the tubular body is performed without the tapered portion, the tubular body smoothly comes into contact with the tapered portion, which leads to reduction in a press-fitting load.

When press-fitting of the tubular body is performed without the tapered portion, the tubular body may be externally fitted to the metallic shell in the state where a difference between the inner diameter of the tubular body and the outer diameter of the metallic shell is larger than a design value, depending on the manufacturing tolerances of the tubular body and the metallic shell, which may result in an excessive press-fitting load. Therefore, by providing the tapered portion to reduce the press-fitting load, increase in the press-fitting load due to the manufacturing tolerances can be suppressed.

In the gas sensor of the present invention, a diameter-increased portion and a diameter-reduced portion may be provided at the outer surface of the metallic shell extending from the tapered portion toward a side axially opposite to the tubular body. The diameter-increased portion may have a diameter larger than a maximum outer diameter of the tapered portion. The diameter-reduced portion may be formed (i.e., located) between the tapered portion and the diameter-increased portion and may have a diameter smaller than the maximum outer diameter of the tapered portion. An end portion of the tubular body may be in contact with the diameter-increased portion and may be in non-contact with (i.e., spaced from) the diameter-reduced portion.

For positioning of the tubular body in the depth direction of the press-fitting to the metallic shell, the diameter-increased portion having a diameter larger than the maximum outer diameter of the tapered portion may be provided at the outer surface of the metallic shell. In this case, a fillet portion is formed at the contact portion between the tapered portion and the diameter-increased portion due to metal working, and the press-fitted tubular body comes into contact with the fillet portion before reaching the diameter-increased portion, which makes the positioning unstable.

By providing the diameter-reduced portion between the tapered portion and the diameter-increased portion, the end portion of the tubular body reliably comes into contact with the diameter-increased portion of the metallic shell without interference with the fillet portion, whereby the positioning of the tubular body can be reliably performed.

In the gas sensor of the present invention, a portion, of the tapered portion, extending toward the tubular body relative to the portion tightly fitted to the tubular body may be separated from the tubular body.

According to this gas sensor, since only a part of the tapered portion is press-fitted into the tubular body, the press-fitting load can be further reduced.

According to the present invention, it is possible to reduce a press-fitting load when a tubular body made of metal is externally fitted to a metallic shell that holds a gas sensor element.

BRIEF DESCRIPTION OF THE DRAWINGS

Illustrative aspects of the invention will be described in detail with reference to the following figures wherein.

DETAILED DESCRIPTION OF EXEMPLARY EMBODIMENTS OF THE INVENTION

Hereinafter, an embodiment of the present invention will be described.

Figure 1:
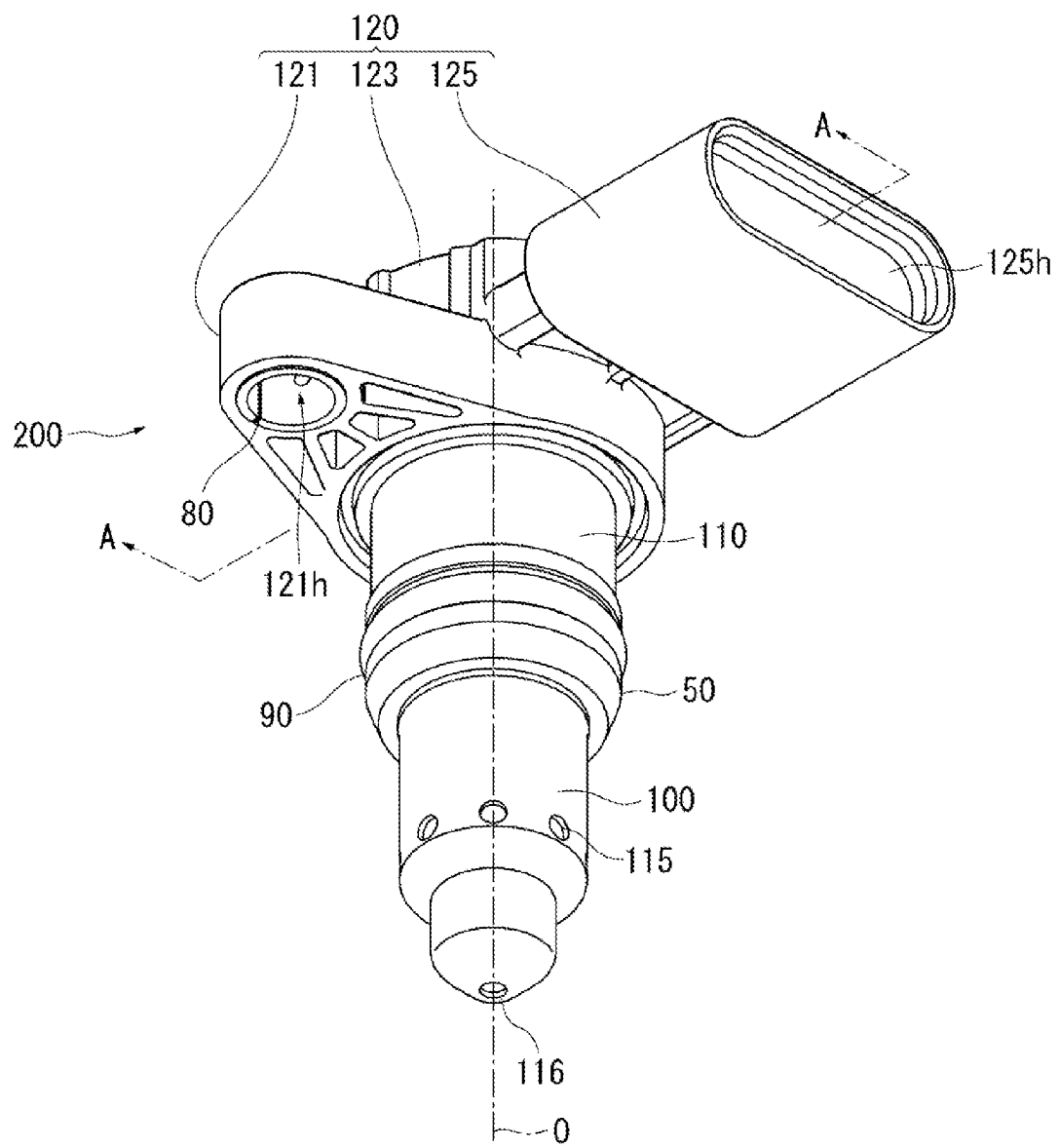
FIG. 1 is a perspective view showing a structure of a gas sensor according to an embodiment of the present invention.
Figure 2:
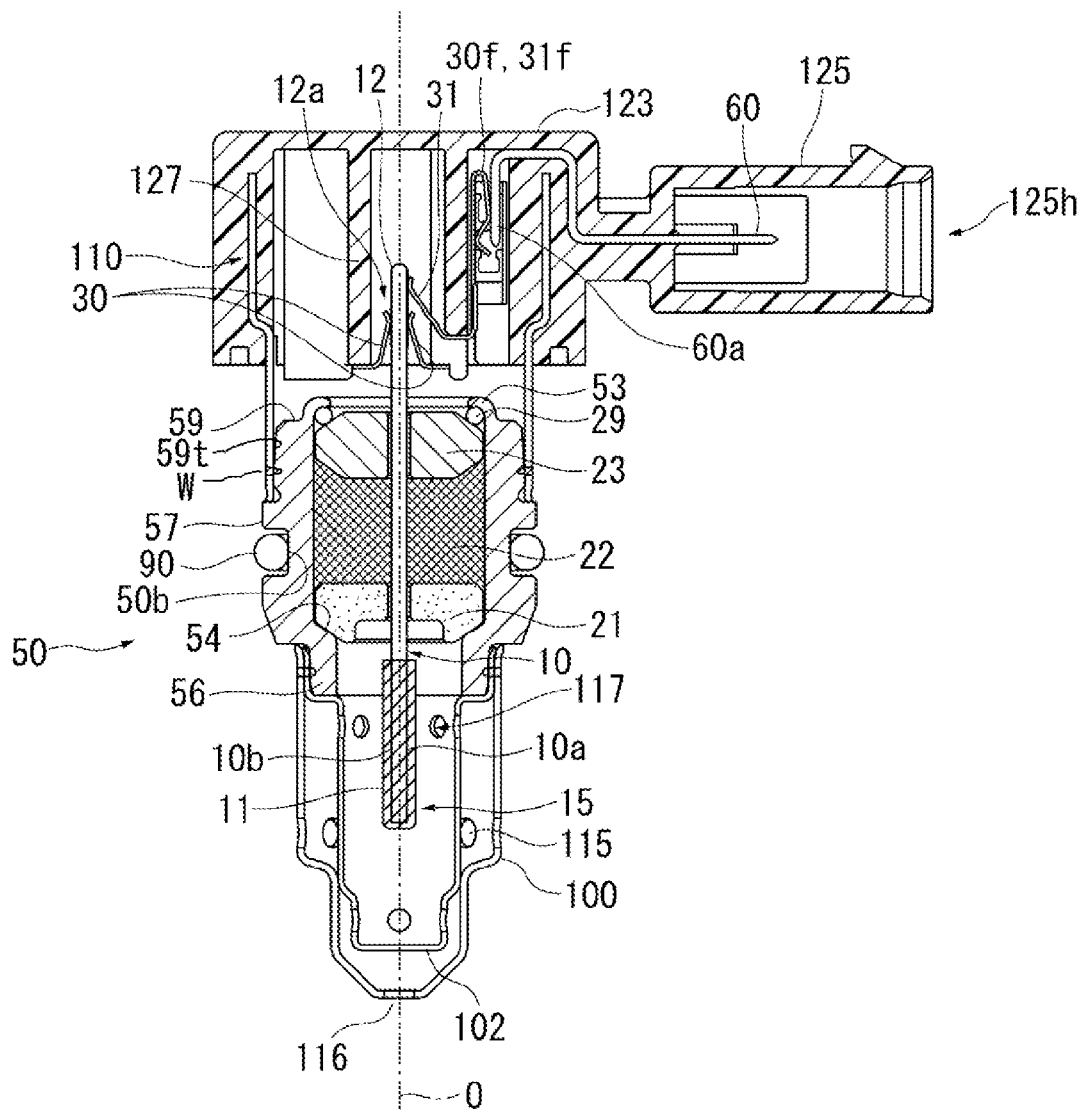
FIG. 2 is a cross-sectional view taken along a line A-A in FIG. 1.
Figure 3:
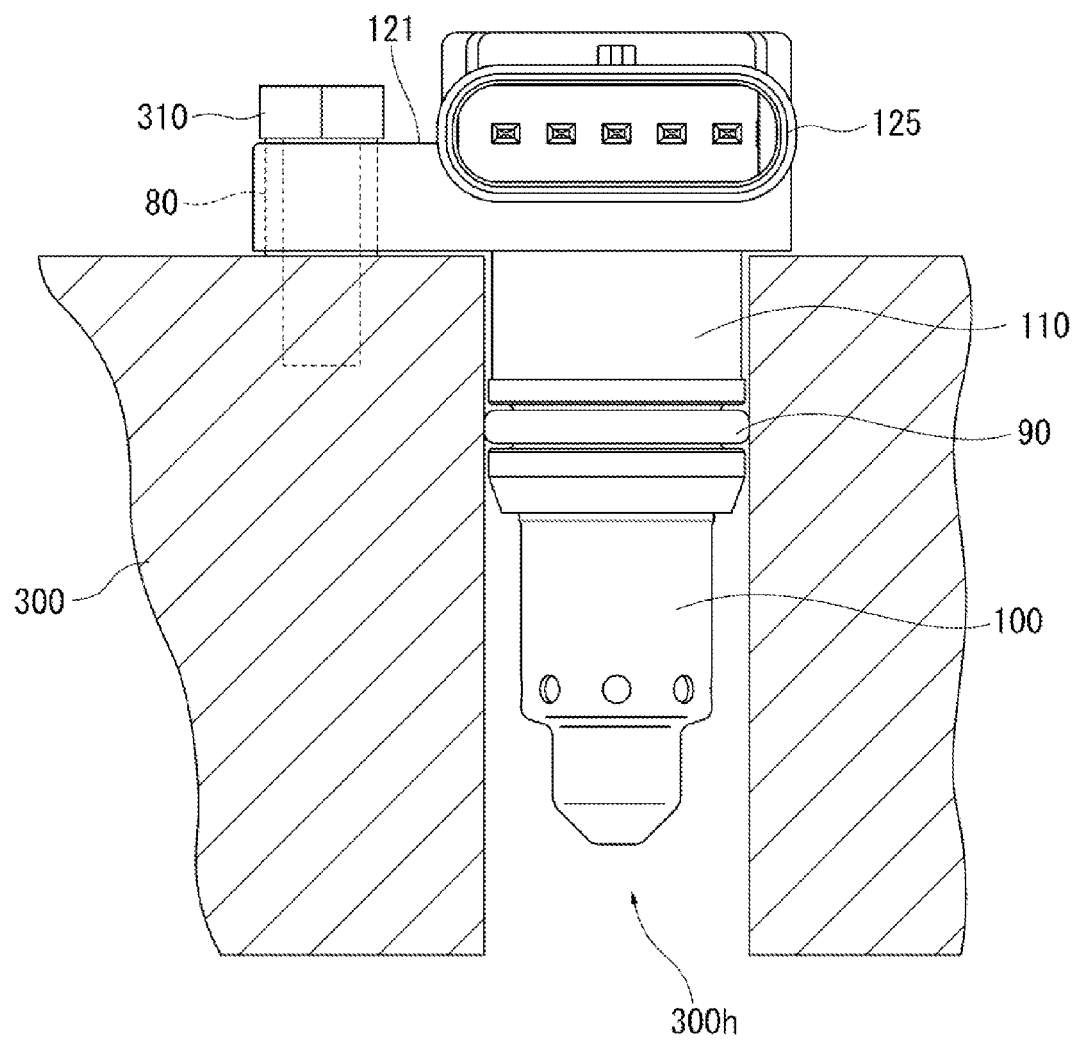
FIG. 3 is a view showing a state in which the gas sensor is mounted to a mounting target.

FIG. 1 is a perspective view of a gas sensor 200 according to an embodiment of the present invention. FIG. 2 is a cross-sectional view taken along a line A-A in FIG. 1. FIG. 3 shows a state in which the gas sensor 200 is mounted to a mounting target 300. The perspective view of FIG. 1 is from below (i.e., looking up toward) the gas sensor 200.

In the following description, the direction of an axis O (shown by an alternate long and short dash line) of a gas sensor element 10 is illustrated as an up-down direction, a side toward a rear end portion 12 of the gas sensor element 10 is referred to as a rear side of the gas sensor element 10 (and the gas sensor), and a side toward a detection portion 11 of the gas sensor element 10, which is opposite to the rear side (refer to FIG. 2), is referred to as a front side of the gas sensor element 10 (and the gas sensor). In addition, the direction perpendicular to the direction of the axis O is referred to as a "radial direction" as appropriate.

In FIG. 2, for the sake of convenience, only three connection terminals 30, 31 are shown, and only one connector terminal 60 is shown. However, actually, a plurality of (five) connection terminals 30, 31 and a plurality of (five) connector terminals 60 are provided in the embodiment of the present invention.

As shown in FIG. 1, the gas sensor 200 includes: a gas sensor element 10 (not shown); an outer protector 100 which covers the detection portion 11 of the gas sensor element 10; a metallic shell 50 which holds the gas sensor element 10; a base portion 120 which is disposed on the rear side of the metallic shell 50 and is made of a polymer material; and a sleeve 110 made of metal, which connects the metallic shell 50 to the base portion 120.

The sleeve 110 corresponds to a "tubular body" described in claims.

The base portion 120 includes: a cylindrical main body portion 123, the rear end of which is closed; one semicircular flange portion 121 which extends radially outward from one side surface of the main body portion 123; and a substantially rectangular connector portion 125 which extends radially outward from another side surface of the main body portion 123. The flange portion 121 and the connector portion 125 are disposed at positions about 90 degrees different from each other in the circumferential direction of the main body portion 123. The main body portion 123, the flange portion 121, and the connector portion 125 are integrally formed of an insulating polymer material (resin) having excellent moldability, such as PPS (polyphenylene sulfide). The connector portion 125 is a male connector having an opening 125h facing radially outward, and allows a mating connector (in this example, a female connector) of an external device to be radially inserted in and removed from the opening 125h.

One mounting hole 121h is opened through the flange portion 121, and a cylindrical collar 80 made of metal is insert-molded in contact with the inner surface of the mounting hole 121h so as to be integrally fixed. As shown in FIG. 3, a screw 310 is inserted through the collar 80, and the screw 310 is screwed into a screw hole provided in a mounting target 300 (e.g., an intake system of an internal combustion engine), whereby the gas sensor 200 can be mounted to the mounting target 300.

A recessed groove 50b (refer to FIG. 2) is formed in the metallic shell 50 along the circumferential direction, and a seal member (O-ring) 90 is externally fitted to the recessed groove 50b. Therefore, when the gas sensor 200 is inserted from the front end side thereof into an opening 300h of the mounting target 300 and mounted to the mounting target 300, the seal member 90 is crushed at the wall surface of the opening 300h of the mounting target 300 and seals a gap between the mounting target 300 and the gas sensor 200 (metallic shell 50).

Meanwhile, the base portion 120 is insert-molded on the rear side of the sleeve 110 so as to be integrated with the sleeve 110.

Further, a plurality of gas introduction holes 115 are provided at the side surface of the outer protector 100, and one gas discharge hole 116 is provided in the center of the front end of the outer protector 100.

Next, the respective components of the gas sensor 200 will be described in more detail with reference to FIG. 2.

The gas sensor element 10 is, as is generally known, a laminate having a substantially prismatic shape extending in the direction of the axis O, in which a detection element for detecting the concentration of oxygen and a heater body for heating the detection element to promote activation of the detection element are bonded together. The detection element has a configuration in which a solid electrolyte containing zirconia as a main component and a pair of electrodes each containing platinum as a main component are laminated via an insulating layer in a part of which a hollow measurement chamber is formed. More specifically, the detection element includes: an oxygen pump cell in which one electrode of the pair of electrodes formed on both surfaces of the solid electrolyte is exposed to the outside and the other electrode of the pair of electrodes is disposed in the measurement chamber; and an oxygen concentration measurement cell in which one electrode of the pair of electrodes formed on both surfaces of the solid electrolyte is disposed in the measurement chamber and the other electrode of the pair of electrodes is disposed in a reference gas chamber. The detection element is configured such that oxygen in the measurement chamber is pumped out or oxygen is pumped from the outside into the measurement chamber, by controlling an electric current flowing across the pair of electrodes of the oxygen pump cell such that an output voltage of the oxygen concentration measurement cell has a predetermined value.

In the oxygen pump cell, the pair of electrodes and a portion of the solid electrolyte sandwiched between these electrodes constitute a detection portion 11 in which a current according to the oxygen concentration flows. On the rear end portion 12 of the gas sensor element 10, five electrode pads 12a for taking an output from the detection element or supplying a power to a heater are formed. In FIG. 2, two of the five pads 12a are disposed on a second surface 10b of the gas sensor element 10 while the remaining three are disposed on a first surface 10a of the gas sensor element 10. These electrode pads 12a are connected to the connection terminals 30, 31.

A ceramic holder 21 is disposed slightly to the front side relative to the center of the gas sensor element 10 in the axial direction. The ceramic holder 21 is made of an insulating ceramic (e.g., alumina) and has a substantially short cylindrical shape. The ceramic holder 21 is disposed in such a state that the gas sensor element 10 is inserted through the ceramic holder 21 and the detection portion 11 protrudes toward the front side relative to the ceramic holder 21.

The gas sensor element 10 is surrounded and held by the tubular metallic shell 50. The metallic shell 50 is made of stainless steel such as SUS430. Specifically, a step portion 54 is formed at the inner circumference of the metallic shell 50, and a front-side peripheral portion of the ceramic holder 21, through which the gas sensor element 10 is inserted, is engaged with the step portion 54. Further, a seal material 22 is loaded into the metallic shell 50 along the inner circumference of the metallic shell 50 from the rear side of the ceramic holder 21 in such a state that the gas sensor element 10 is inserted through the seal material 22. A tubular sleeve 23 is fitted into the metallic shell 50 so as to hold the seal material 22 from the rear side of the seal material 22. An annular crimp packing 29 is disposed on the rear-side outer circumference of the sleeve 23.

Meanwhile, a diameter-reduced rear end portion 59 is formed on the rear-side outer circumference of the metallic shell 50, and a diameter-increased portion 57, the diameter of which is increased stepwise radially outward, is formed on the front side relative to the rear end portion 59. The recessed groove 50b is formed in the diameter-increased portion 57 along the circumferential direction, and the seal member (O-ring) 90 is externally fitted in the recessed groove 50b. Further, a front-end engagement portion 56 is formed on the front side relative to the diameter-increased portion 57. The front-end engagement portion 56 has a diameter smaller than that of the diameter-increased portion 57, and an outer protector 100 and an inner protector 102, which are described later, are engaged with the front-end engagement portion 56. A crimp portion 53 for crimp-holding the gas sensor element 10 in the metallic shell 50 is formed on the rear side of the rear end portion 59.

The crimp portion 53 of the metallic shell 50 is crimped so as to press the sleeve 23 frontward via the crimp packing 29. Being pressed by the crimp portion 53 via the sleeve 23, the seal material 22 is crushed in the metallic shell 50 and tightly fills the metallic shell 50. By means of the seal material 22, the ceramic holder 21 and the gas sensor element 10 are positioned and hermetically held in the metallic shell 50.

Meanwhile, the outer peripheral surface of the detection portion 11 of the gas sensor element 10 is covered with a porous protection layer 15 so as to protect an electrode of the detection portion 11, which is exposed to the outside, from being contaminated or wetted by air intake or the like. The outer protector 100 and the inner protector 102 are fitted to the front-end engagement portion 56 of the metallic shell 50, and fixed thereto by laser welding, thereby to protect the detection portion 11 housed therein. The outer protector 100 has the gas introduction holes 115, and the inner protector 102 has gas introduction holes 117. Further, one gas discharge hole 116 is provided in the center of the front end of the outer protector 100.

The sleeve 110, for example, is made of stainless steel and has a cylindrical shape, the diameter of which is increased at the rear side via a step portion. The base portion 120 is insert-molded into the rear side of the sleeve 110 including the step portion, and the step portion prevents removal of the base portion 120 from the sleeve 110.

The front-side portion of the sleeve 110, which is exposed from the base portion 120, is externally fitted to a tapered portion 59t formed at the rear end portion 59 of the metallic shell 50, and a welded portion W is formed at the tapered portion 59t through all-around laser welding or the like performed from the outside of the sleeve 110. Thus, the base portion 120 is connected (fixed) to the metallic shell 50. The tapered portion 59t will be described later.

The base portion 120 serves as a cover surrounding the rear end portion 12 of the gas sensor element 10, which protrudes to the rear side of the metallic shell 50. Further, the connector terminal 60 electrically connected to the external device is held in the connector portion 125. The connector portion 125 including the connector terminal 60 is formed by insert-molding.

Further, inside the main body portion 123, a separator portion 127 having a substantially box shape and extending toward the front side is formed integrally with the main body portion 123. The separator portion 127 holds the connection terminals 30, 31. Spring pieces 30f, 31f are provided at one ends of the connection terminals 30, 31, respectively, and are electrically connected to end portions 60a of the corresponding connector terminals 60. Thus, the gas sensor element 10 disposed inside the gas sensor 200 is electrically connected to the external device.

Next, a method of connecting the sleeve 110 to the metallic shell 50 will be described with reference to FIGS. 4A to 4D. FIGS. 4A to 4D show process steps for connecting the sleeve 110 to the metallic shell 50 as seen from a cross section along the direction of the axis O.

Figure 4:
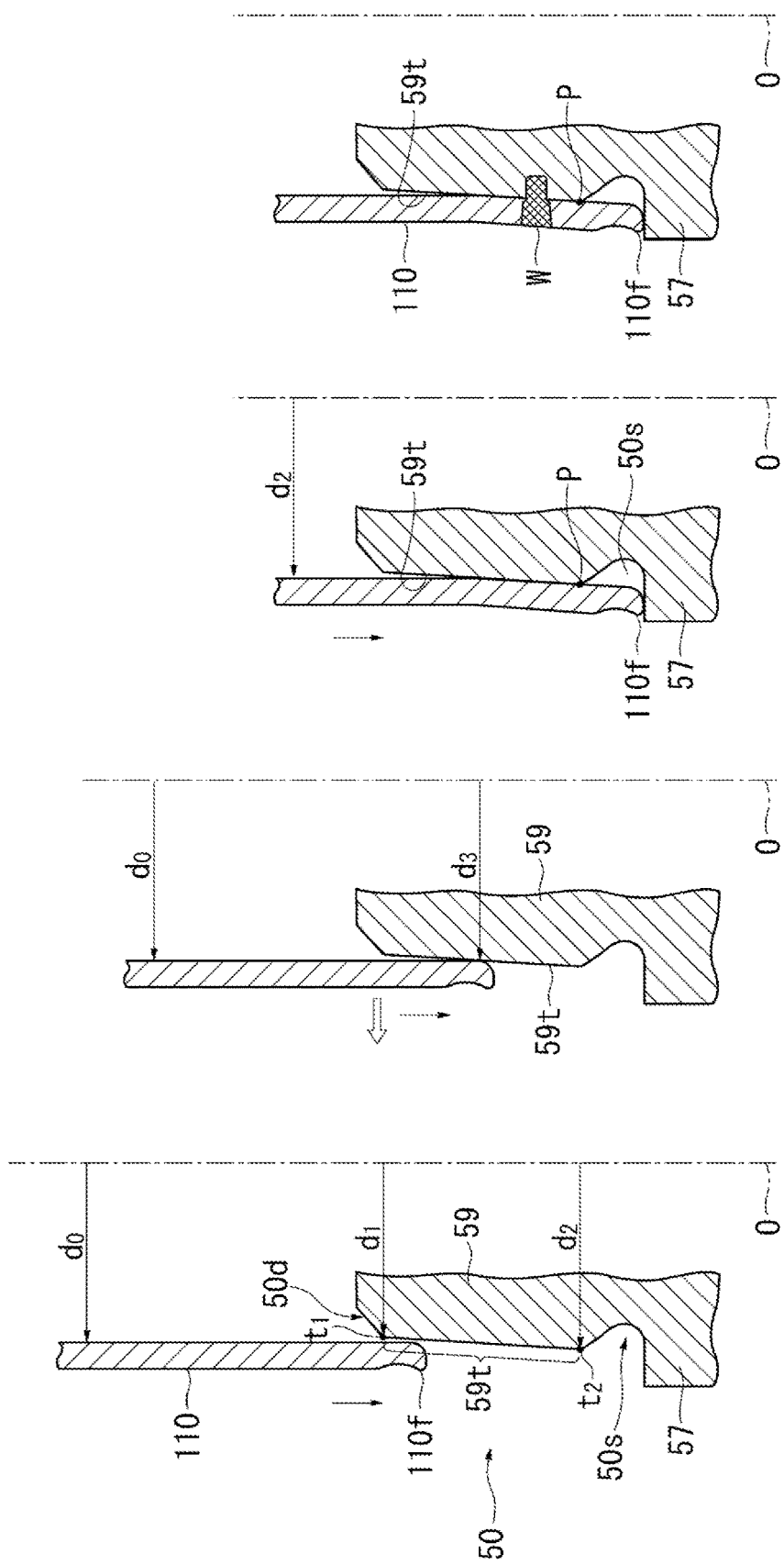
FIGS. 4A to 4D are views showing process steps for connecting a sleeve to a metallic shell.

First, as shown in FIG. 4A, the tapered portion 59t which is narrowed in the radial direction toward the rear side (toward the sleeve 110) is formed at the outer surface of the rear end portion 59 of the metallic shell 50. In the example shown in FIG. 4A, the tapered portion 59t is a linearly tapered portion. A chamfered portion 50d which is further narrowed in the radial direction of the metallic shell 50 is formed on the rear side relative to a rearmost end t1 of the tapered portion 59t. Further, in the present embodiment, with respect to an inner diameter d0 of the sleeve 110 before press-fitted, a minimum outer diameter d1 of the rearmost end t1 of the tapered portion 59t and a maximum outer diameter d2 of a frontmost end t2 of the tapered portion 59t are set so as to satisfy a condition of d1<d0<d2.

The diameter-increased portion 57 and a diameter-reduced portion 50s are formed at the outer surface of the metallic shell 50 extending from the frontmost end t2 of the tapered portion 59t toward the front side (the side axially opposite to the sleeve 110). The diameter-increased portion 57 has a diameter larger than the maximum outer diameter d2 of the tapered portion 59t. The diameter-reduced portion 50s is formed between the tapered portion 59t and the diameter-increased portion 57, and has a diameter smaller than the maximum outer diameter d2 of the tapered portion 59t. The diameter-reduced portion 50s has a cross-sectional shape that is recessed in a semicircular shape.

As the sleeve 110 is press-fitted from the front side thereof to the tapered portion 59t of the metallic shell 50, since d1<d0, the sleeve 110 is in non-contact with the tapered portion 59t in the initial stage of the press-fitting (FIG. 4A). When the outer diameter d3 of the tapered portion 59t becomes equal to d0, the sleeve 110 comes into contact with the tapered portion 59t, and thereafter, the sleeve 110 is press-fitted toward the front side along the surface of the tapered portion 59t, with the diameter thereof being gradually increased (FIG. 4B).

When the front end portion 110f of the sleeve 110 comes into contact with the diameter-increased portion 57 located on the front side relative to the tapered portion 59t of the metallic shell 50, the sleeve 110 is positioned in the depth direction of the press-fitting, and in this state, the press-fitting (temporary fixing) of the sleeve 110 to the metallic shell 50 is ended (FIG. 4C). At this time, the inner diameter of the sleeve 110 is increased to a diameter ranging from a diameter larger than d3 to a diameter equal to d2. Thus, a portion P, of the sleeve 110, on the rear side relative to the front end portion 110f of the sleeve 110 is in contact with a portion, of the tapered portion 59t of the metallic shell 50, having an outer diameter ranging from d3 to d2.

Next, the press-fitted portion of the sleeve 110 is externally subjected to all-around welding at a position on the rear side relative to the portion P to form the welded portion W, thereby completing the fixing process (FIG. 4D).

As described above, since the tapered portion 59t is formed at the outer surface of the rear end portion 59 of the metallic shell 50, when the sleeve 110 is externally fitted (press-fitted) to the metallic shell 50, the diameter of the sleeve 110 is gradually increased along the surface of the tapered portion 59t. Therefore, in contrast to the case where press-fitting of the sleeve 110 is performed without the tapered portion (by sliding the sleeve 110 on the outer surface extending in parallel to the direction of the axis O), the sleeve 110 smoothly comes into contact with the tapered portion 59t, which leads to reduction in the press-fitting load.

Further, in the case where press-fitting of the sleeve 110 is performed without the tapered portion, the sleeve 110 may be externally fitted to the metallic shell 50 in the state where a difference between the inner diameter of the sleeve 110 and the outer diameter of the metallic shell 50 is larger than a design value, depending on the manufacturing tolerances of the sleeve 110 and the metallic shell 50, which may result in an excessive press-fitting load. Therefore, by providing the tapered portion 59t to reduce the press-fitting load, increase in the press-fitting load due to the manufacturing tolerances can be suppressed.

The welded portion W needs to be formed at the position of the tapered portion 59t. The reason is as follows. Since the distance between the outer surface of the metallic shell 50 and the inner surface of the sleeve 110 is great in a portion other than the tapered portion 59t, if welding is performed at the portion other than the tapered portion 59t, defective welding may occur.

When the condition of d1<d0<d2 is satisfied, the sleeve 110 is in non-contact with the tapered portion 59t in the initial stage of the press-fitting, whereby the press-fitting load can be further reduced. Further, when the condition of d1<d0<d2 is satisfied, even if d0 becomes smaller than the design value due to the manufacturing tolerances, since the portion that satisfies d1<d0 is present in the tapered portion 59t, the sleeve 110 can be press-fitted along the surface of the tapered portion 59t, thereby suppressing increase in the press-fitting load due to the manufacturing tolerances.

However, the condition of d1<d0<d2 is not essential. Even when d1>d0, the diameter of the sleeve 110 is gradually increased along the surface of the tapered portion 59t after the sleeve 110 has come into contact with the tapered portion 59t. Therefore, also in this case, reduction in the press-fitting load can be achieved.

Figure 5:
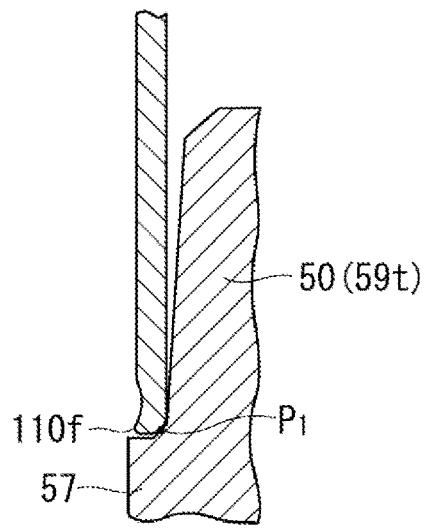
FIG. 5 is a view showing a positional relation between a tapered portion and the sleeve in a case where a diameter-reduced portion is not provided at the outer surface of the metallic shell.

In the present embodiment, for positioning of the sleeve 110 in the depth direction of the press-fitting to the metallic shell 50, the diameter-increased portion 57 having a diameter larger than the maximum outer diameter d2 of the tapered portion 59t is provided at the outer surface of the metallic shell 50. In this case, as shown in FIG. 5, a fillet portion P1 is formed at the contact portion between the tapered portion 59t and the diameter-increased portion 57 due to metal working, and the press-fitted sleeve 110 comes into contact with the fillet portion P1 before reaching the diameter-increased portion 57, which makes the positioning unstable.

By providing the diameter-reduced portion 50s between the tapered portion 59t and the diameter-increased portion 57, the end portion of the sleeve 110 reliably comes into contact with the diameter-increased portion 57 of the metallic shell 50 without interference with the fillet portion, whereby the positioning of the sleeve 110 can be reliably performed.

Further, in the present embodiment, as shown in FIG. 4D, a portion, of the tapered portion 59t, extending toward the sleeve 110 side relative to the portion tightly fitted to the sleeve 110 (a portion opposite to the metallic shell 59 in the direction of the axis O) is separated from the sleeve 110.

Therefore, only a part of the tapered portion 59t is press-fitted into the sleeve 110, whereby the press-fitting load can be further reduced.

The tapered portion 59t is a line segment between points t1 and t2 on a straight line including the portion P which is the contact point between the metallic shell 50 (tapered portion 59t) and the sleeve 110 (FIG. 4A).

Figure 6:
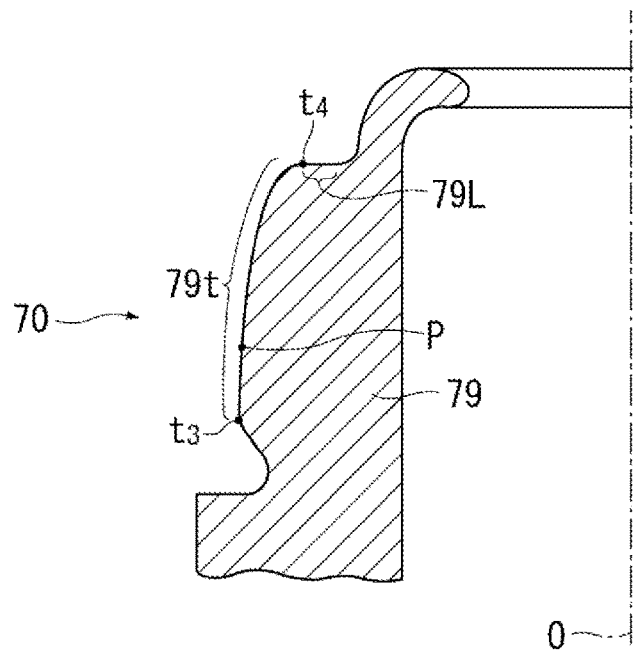
FIG. 6 is a cross-sectional view showing a tapered portion as a curved taper.
Figure 7C:
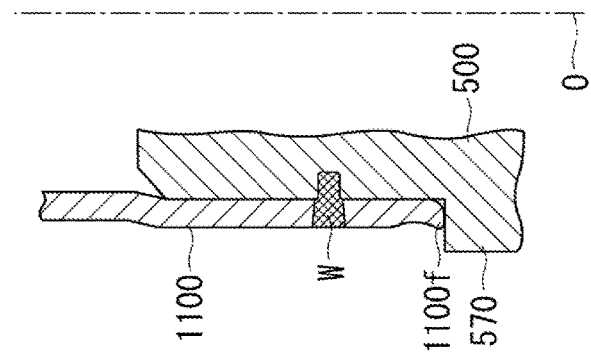
FIGS. 7A to 7C are views showing process steps for connecting a sleeve to a metallic shell in a conventional gas sensor.
Figure 7B:
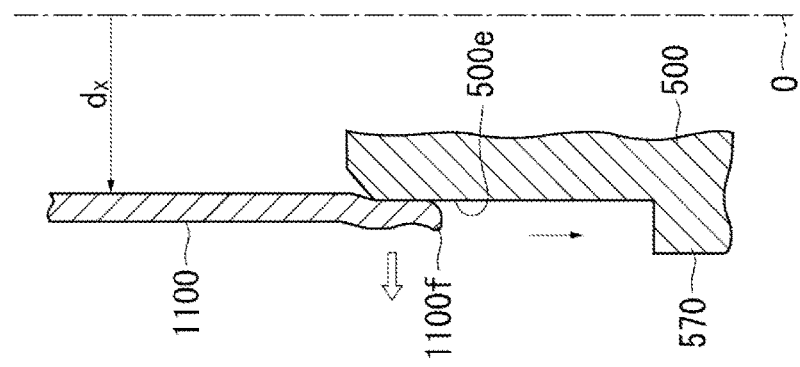
Figure 7A:
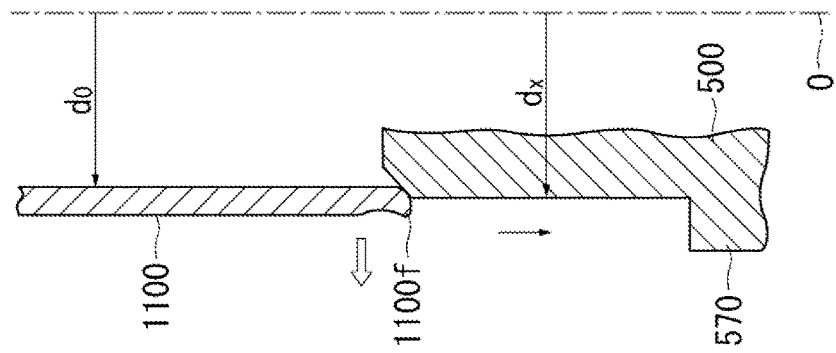

Further, as shown in FIG. 6, in the case where a tapered portion 79t formed at the rear end portion 79 of the metallic shell 70 is a curved tapered portion, an inflection point on the front side (the side axially opposite to the sleeve 110) relative to a portion P on a curved line including the contact point (portion) P with the sleeve 110 is regarded as t3, and a contact point between the curved line and a horizontal portion 79L perpendicular to the axis O on the rear side (the sleeve 110 side) relative to the portion P is regarded as t4. Then, a curved line between the points t3 and t4 is regarded as the tapered portion 79*t*.

The present invention is not limited to the embodiment described above, and the invention encompasses various modifications and equivalents within the spirit and scope of the present invention.

For example, in addition to the sleeve 110, a protector (the outer protector 100 and the inner protector 102) may be used as a tubular body. In this case, since the protector is externally fitted to the front side of the metallic shell 50, the front-end engagement portion 56 is formed to be a tapered portion that is radially narrowed toward the front side.

In the embodiment described above, the base portion (cover) 120 made of a polymer material is connected to the rear end of the sleeve 110, and a portion of the gas sensor element 10, which protrudes to the rear side relative to the metallic shell 50, is covered with the sleeve (tubular body) 110. However, like the gas sensor of the Patent Document 1, for example, the sleeve 110 may cover the entirety of the rear end of the gas sensor element 10.

In the embodiment described above, the strip-shaped sensor element having a quadrilateral (rectangular) transverse cross-section is adopted. However, the sensor element used in the gas sensor of the present invention may have a square transverse cross-section, or may be a tubular sensor element. Further, although the gas sensor of the present invention is embodied as a full-range air-fuel ratio sensor, the gas sensor can also be embodied as other gas sensors.

DESCRIPTION OF REFERENCE NUMERALS

10: gas sensor element
11: detection portion
50, 70: metallic shell
57: diameter-increased portion
59*t*, 79*t*: tapered portion
50*s*: diameter-reduced portion
110: tubular body (sleeve)
110*f*: end portion of tubular body
200: gas sensor O: axis
W: welded portion
d2: maximum outer diameter of tapered portion

What is claimed is:

1. A gas sensor comprising:
   a gas sensor element extending in a direction of an axis, and including, at a front side thereof, a detection portion configured to detect a specific gas component in a measurement target gas;
   a metallic shell surrounding a radial periphery of the gas sensor element, and holding the gas sensor element; and
   a tubular body made of metal, the tubular body being welded in a state of being externally fitted to a front side or a rear side of the metallic shell so as to extend beyond a distal edge of the metallic shell, wherein
   the tubular body is tightly fitted to a tapered portion that is provided at an outer surface of the metallic shell and is radially narrowed toward the distal edge of the metallic shell, and the tubular body is welded at the tapered portion.

2. The gas sensor according to claim 1, wherein
   a diameter-increased portion and a diameter-reduced portion are provided at the outer surface of the metallic shell extending from the tapered portion toward a side axially opposite to the tubular body, the diameter-increased portion having a diameter larger than a maximum outer diameter of the tapered portion, the diameter-reduced portion being located between the tapered portion and the diameter-increased portion and having a diameter smaller than the maximum outer diameter of the tapered portion, and
   an end portion of the tubular body is in contact with the diameter-increased portion and is spaced from the diameter-reduced portion.

3. The gas sensor according to claim 1, wherein a portion of the tapered portion extending toward the distal edge of the metallic shell from the portion of the tapered portion tightly fitted to the tubular body is separated from the tubular body.

4. The gas sensor according to claim 2, wherein a portion of the tapered portion extending toward the distal edge of the metallic shell from the portion of the tapered portion tightly fitted to the tubular body is separated from the tubular body.

* * * * *